(12) United States Patent
Leeflang et al.

(10) Patent No.: US 11,033,713 B2
(45) Date of Patent: Jun. 15, 2021

(54) CATHETER HUBS AND VALVES FOR MINIMIZING EMBOLIC POTENTIAL

(71) Applicant: AUST DEVELOPMENT, LLC, Palo Alto, CA (US)

(72) Inventors: Stephen Arie Leeflang, Sunnyvale, CA (US); Christian Scott Eversull, Palo Alto, CA (US)

(73) Assignee: AUST DEVELOPMENT, LLC, Palo Alto, CA (US)

( * ) Notice: Subject to any disclaimer, the term of this patent is extended or adjusted under 35 U.S.C. 154(b) by 793 days.

(21) Appl. No.: 15/752,826

(22) PCT Filed: Aug. 6, 2015

(86) PCT No.: PCT/US2015/043886
§ 371 (c)(1),
(2) Date: Feb. 14, 2018

(87) PCT Pub. No.: WO2016/036468
PCT Pub. Date: Mar. 10, 2016

(65) Prior Publication Data
US 2018/0304041 A1    Oct. 25, 2018

Related U.S. Application Data

(60) Provisional application No. 62/044,325, filed on Sep. 1, 2014, provisional application No. 62/174,521, filed on Jun. 12, 2015.

(51) Int. Cl.
*A61M 25/00* (2006.01)
*A61M 39/06* (2006.01)

(52) U.S. Cl.
CPC ........ *A61M 25/0097* (2013.01); *A61M 39/06* (2013.01); *A61M 39/0606* (2013.01); *A61M 2039/0633* (2013.01); *A61M 2039/0686* (2013.01)

(58) Field of Classification Search
CPC .............. A61M 25/0097; A61M 39/06; A61M 39/0606; A61M 2039/0663
See application file for complete search history.

(56) References Cited

U.S. PATENT DOCUMENTS

| 2002/0010425 | A1* | 1/2002 | Guo ...................... A61M 39/06 604/167.04 |
| 2011/0004223 | A1* | 1/2011 | Leeflang ........... A61M 25/0014 606/108 |

* cited by examiner

*Primary Examiner* — Tiffany Legette
(74) *Attorney, Agent, or Firm* — William A. English; Vista IP Law Group LLP (57) ABSTRACT

A hub is provided for a sheath, catheter, or other tubular device that includes a tubular body comprising a proximal end, a distal end, and a hub passage extending between the proximal end and the distal end; a valve mounted in the tubular body adjacent the proximal end comprising a proximal surface adjacent the proximal end and a distal surface adjacent an intermediate region of the hub passage; a side port comprising a first end coupled to an outer surface of the tubular body adjacent the intermediate region, a second outer end, and a port passage extending between the second end and the first end and communicating with the intermediate region of the hub passage; and a guide element in the side port adjacent the first end for directing fluid introduced into the second end through the port passage towards the distal surface of the valve.

11 Claims, 6 Drawing Sheets

CATHETER HUBS AND VALVES FOR MINIMIZING EMBOLIC POTENTIAL

This application claims benefit of U.S. provisional application Ser. No. 62/044,325, filed Sep. 1, 2014, and 62/174,521, filed Jun. 12, 2015, the entire disclosures of which are expressly incorporated by reference herein.

FIELD OF THE INVENTION

The present invention relates generally to apparatus and methods for delivering instruments and/or agents during a medical procedure, and, more particularly, to hubs for guide sheaths, catheters, and other tubular devices for accessing body lumens and/or for delivering instruments into body lumens of a patient, and to methods for making and using them.

BACKGROUND

Catheters are elongate tubular devices sized for introduction into body passages and cavities of a patient, such as a patient's cardiovascular system. A catheter may include one or more lumens intended for passing various other devices, agents, and/or fluids into a body lumen or cavity accessed by the catheter.

When placed in the cardiovascular system, such catheters generally include a hemostatic valve to reduce blood loss. In addition to minimizing blood loss during a procedures, it may also be important to minimize air ingress into the catheter and/or introduction of air into the cardiovascular system. This is of particular importance when catheters are place into the arterial system most especially when catheters are placed proximal of the brain, e.g. in the left side of the heart. In such cases, introduced air may act as an embolic particle potentially leading to stroke.

An example of such a procedure is the introduction of a deflectable sheath across the interatrial septum, e.g., for the purpose of performing an ablation procedure. In such procedures, a catheter or sheath is generally flushed with saline prior to introduction in order to eliminate air from the system. Effective flushing may eliminate substantially all air from the catheter before introduction into the patient's vasculature. However, certain catheter hub and/or valve constructions may permit small, but potentially clinically relevant amounts of air to remain in the catheter after flushing.

Therefore, apparatus that may reduce the risk of introducing air into a patient's body would be useful.

SUMMARY

The present invention is directed generally to apparatus and methods for delivering instruments and/or agents during a medical procedure. More particularly, the present invention is related to hubs for guide sheaths, catheters, and other tubular devices for accessing and/or delivering instruments into body lumens of a patient, and to methods for making and using them.

In accordance with one embodiment, a hub is provided for a sheath, catheter, or other tubular device that includes a tubular body comprising a proximal end, a distal end, and a hub passage extending between the proximal end and the distal end; a valve mounted in the tubular body adjacent the proximal end comprising a proximal surface adjacent the proximal end and a distal surface adjacent an intermediate region of the hub passage; a side port comprising a first end coupled to an outer surface of the tubular body adjacent the intermediate region, a second outer end, and a port passage extending between the second end and the first end and communicating with the intermediate region of the hub passage; and a guide element in the side port adjacent the first end for directing fluid introduced into the second end through the port passage towards the distal surface of the valve.

In exemplary embodiments, the guide element may include a ramped surface adjacent an outlet of the side port, e.g., that extends helically relative to a central axis of the side port, a ramped surface including an inner edge adjacent the hub passage oriented to deflect fluid towards the proximal end within the hub passage, or a flow divider extending across the outlet for dividing flow of fluid introduced into the second end through the port passage into the hub passage. In one embodiment, the flow divider may include first and second spiral surfaces dividing the outlet into first and second openings. In another embodiment, the flow divider may include a single leading edge and a pair of ramped surfaces communicating with first and second openings.

In accordance with another embodiment, a hub is provided for a sheath, catheter, or other tubular device that includes a tubular body comprising a proximal end, a distal end, a hub passage extending between the proximal end and the distal end, and a longitudinal axis between the proximal end and the distal end; a valve mounted in the tubular body adjacent the proximal end for providing a substantially fluid-tight seal while accommodating inserting an instrument into the proximal end into the hub passage, the valve comprising a proximal surface adjacent the proximal end and a distal surface adjacent an intermediate region of the hub passage; and a side port comprising a first end coupled to an outer surface of the tubular body adjacent the intermediate region, a second outer end, and a port passage extending between the second end and the first end and communicating with the intermediate region of the hub passage, wherein the port passage comprises a first inner region adjacent the first end defining a first port axis and a second outer region adjacent the second end defining a second port axis, the second port axis defining an acute second angle relative to the longitudinal axis and proximal end of the tubular body, the first port axis defining a first angle relative to the longitudinal axis that is less acute than the second angle.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION OF THE EXEMPLARY EMBODIMENTS

Figure 1:
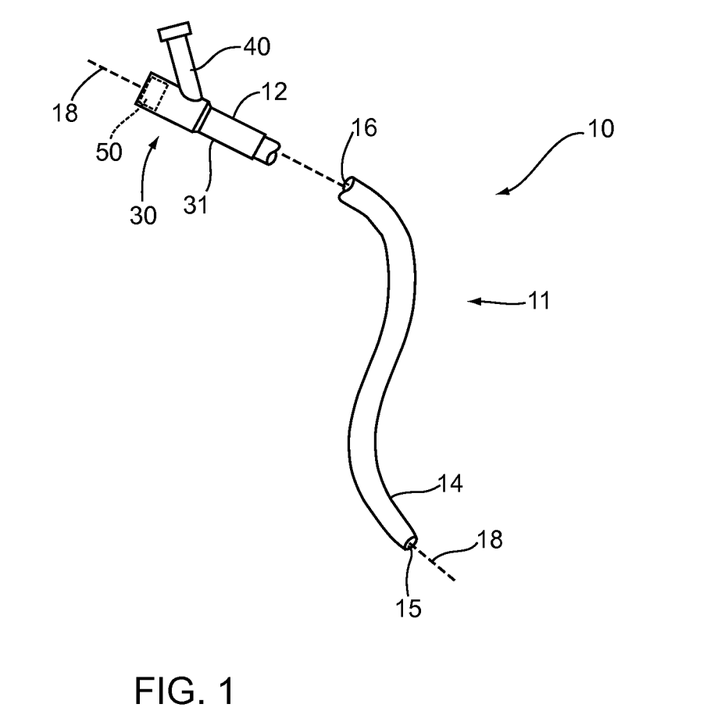
FIG. 1 is a perspective view of an exemplary embodiment of a tubular device, including a hub on a proximal end thereof.

Turning to the drawings, FIG. 1 shows an exemplary embodiment of an apparatus 10 for accessing a body lumen (not shown) and/or for delivering one or more fluids, agents, and/or instruments (also not shown) within a body lumen. In exemplary embodiments, the apparatus 10 may be a guide catheter, a procedure catheter, a sheath, an imaging device, or other tubular device sized for introduction into a body lumen, such as a vessel within a patient's vasculature, a passage within a patient's gastrointestinal tract, urogenital tract, reproductive tract, respiratory tract, lymphatic system, and the like.

Generally, the apparatus 10 includes an elongate tubular member 11 including a proximal end 12, a distal end 14 sized for introduction into a body lumen, a lumen 16 extending between the proximal and distal ends 12, 14 along a central longitudinal axis 18, and a handle or hub 30 on the proximal end 12 including one or more valves (one valve 50 shown in phantom) for allowing one or more devices to be introduced and/or fluids to be infused into the lumen 16 and a side port 40, while minimizing loss of blood from the apparatus 10 and/or ingress of air. Optionally, the apparatus 10 may include one or more additional lumens (not shown), which may be disposed concentrically around, side-by-side with, or otherwise adjacent the lumen 16 and/or ports (also not shown) on the hub 30 communicating with respective lumen(s). The lumen 16 may be sized for receiving a guide wire, procedure catheter, cardiac lead, needle, or other instrument (not shown), and/or for delivering fluids or other flowable agents or materials therethrough, as described further below.

Figure 2:
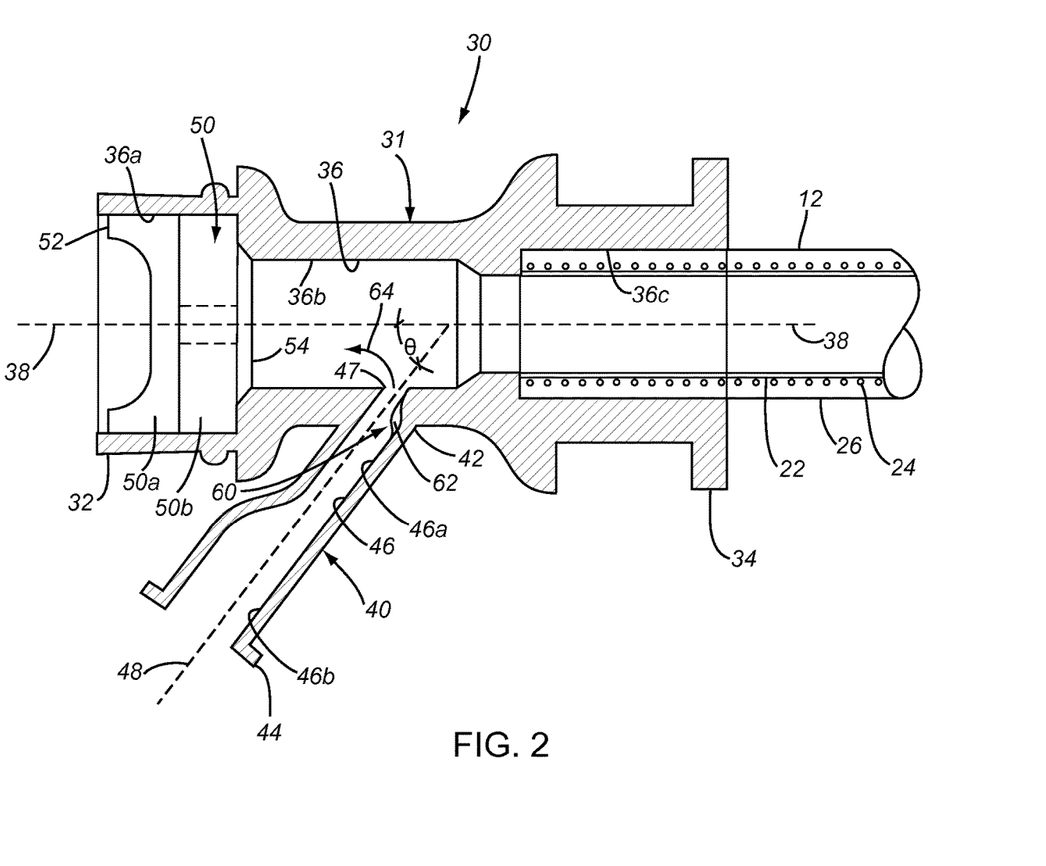
FIG. 2 is a cross-sectional side view of an exemplary embodiment of a hub that may be provided on the proximal end of the tubular device of FIG. 1.

As can be seen in FIG. 2, the tubular member 11 may be constructed from one or more layers, e.g., an inner liner 22 surrounding the lumen 16, a reinforcing layer 24 surrounding the inner liner 22, and an outer layer 26. Optionally, one or more coatings (not shown) may be applied to the inner surface of the inner liner 22. In an exemplary embodiment, a hydrophilic coating, such as Polyvinylpyrrolidone, may be sprayed or otherwise applied onto the surface of the inner liner 22 during fabrication to provide a lubricious inner surface for the lumen 16 of the tubular member 11. Exemplary materials and methods for making the tubular member 11 are disclosed in U.S. Pat. Nos. 7,553,387, 7,550,053, 8,070,898, 8,454,578, 8,673,100, and 8,927,048. The entire disclosures of these references are expressly incorporated by reference herein.

The layers of the tubular member 11 may be attached to one another, e.g., by laminating, adhering, adhesive bonding, ultrasonic welding, reflowing or other heating, and the like. The construction of the tubular member 11 may be substantially uniform or may vary between the proximal and distal ends 12, 14, e.g., by varying the inner liner, 22, reinforcing layer 24, and/or outer layer 26 along the length of the tubular member 11. Optionally, the inner liner 22, reinforcing layer 24, and/or outer layer 26 may include one or more sublayers (not shown), which may vary in construction in various portions of the tubular member 11.

In one exemplary embodiment, the proximal end 12 may be substantially rigid or semi-rigid, e.g., providing sufficient column strength to allow the tubular member 11 to be pushed from the proximal end 12, while the distal end 14 may be substantially flexible or semi-rigid. Thus, the distal end 14 of the tubular member 11 may be advanced or otherwise manipulated within a patient's body from the hub 30 and/or proximal end 12 without substantial risk of buckling and/or kinking.

In exemplary embodiments, the tubular member 11 may have an outer diameter between about half and twenty millimeters (0.5-20 mm) or between about one and five millimeters (1-5 mm), and a length between about five and one hundred fifty centimeters (5-150 cm). The inner liner 22 may have a wall thickness between about 0.0001-0.01 inch (0.0025-0.25 mm) and the outer layer 26 may have a wall thickness between about 0.0005-0.2 inch (0.0127-5.08 mm).

The outer layer 26 may have a substantially homogenous construction between the proximal and distal ends 12, 14. Alternatively, the construction may vary along the length of the apparatus 10 to provide desired properties. For example, the outer layer at or adjacent the proximal end 12 may be substantially rigid or semi-rigid, e.g., providing sufficient column strength to facilitate the apparatus 10 being pushed from the proximal end 12. In addition, the reinforcing layer 24 or other material in the outer layer 26 may allow the apparatus 10 to be twisted from the proximal end 12, e.g., to rotate the distal end 14 within a patient's body. Thus, the distal end 14 of the apparatus 10 may be manipulated within a patient's body from the proximal end 12 without substantial risk of buckling and/or kinking. Optionally, the outer layer at or adjacent the distal end 14 may be substantially flexible or semi-rigid, e.g., to allow the distal end 14 to bend easily or otherwise be advanced through tortuous anatomy and/or provide a substantially atraumatic distal tip 15. Furthermore, the outer layer may have one or more transition regions along its length, transitioning from one desired construction to another. Exemplary outer layers that may be included in the apparatus 10 and methods for making them are disclosed in U.S. Pat. Nos. 4,478,898, 4,863,442, 5,217, 440, 5,254,107, 5,676,659, 5,811,043, 5,836,926, 6,004,310, 6,669,886, 6,837,890, and 6,945,970. The entire disclosures of these references are expressly incorporated by reference herein.

Optionally, the distal end 14 may include a tapered, rounded, or otherwise shaped distal tip 15, e.g., to provide a substantially atraumatic tip and/or to facilitate advancement or navigation through various anatomy. In addition or alternatively, the distal end 14 may include one or more therapeutic and/or diagnostic elements, e.g., one or more balloons, stents, sensors, electrodes, steering mechanisms, imaging devices, needles, and the like (not shown), depending upon the particular intended application for the apparatus 10. Further, in addition or alternatively, the distal end 14 may be deflectable or otherwise redirectable (not shown), e.g., to facilitated navigation within the body.

Returning to FIG. 2, an exemplary embodiment of a hub 30 is shown that generally includes an elongate main hub portion or tubular body 31 and a side port 40 extending transversely from the tubular body 31. The tubular body 31 includes a proximal end 32, a distal end 34, and a hub passage 36 extending between the proximal and distal ends 32, 34, thereby defining a central longitudinal axis 38. The tubular body 31 may have a substantially uniform outer diameter or cross-section or may include one or more features, e.g., annular rings or ridges, that may provide structural support for the hub 30, attachment to handle (not shown) and/or to facilitate holding and/or manipulating the apparatus 10 during use.

In the embodiment shown, the hub passage 36 includes a valve recess 36a adjacent the proximal end 32, an intermediate region 36b, and a distal region 36c aligned generally along the longitudinal axis 38. The hub passage 36 may have a substantially uniform diameter or other cross-section between the proximal and distal ends 32, 34 or may have different cross-sections in the different regions. For example, the valve recess 36a may have a larger inner diameter than the intermediate region 36b sized to receive the valve 50 and/or the distal region 36c may have a larger diameter than the intermediate region 36b, e.g., to accommodate receiving the proximal end 12 of the tubular member 11, as described further below. For example, a proximal end of a catheter shaft may be inserted into the distal region 36c and/or otherwise coupled to the distal end 34. In one embodiment, the distal end 34 may be coupled to a handle of a deflectable sheath (not shown), and a catheter shaft may be inserted through the sheath handle, into the distal region 36c, and secured to the hub 30.

In addition or alternatively, the hub passage 36, and in particular, the intermediate region 36a of the hub passage 36 may include a coating, e.g., to increase lubricity and/or reduce surface tension. For example, the intermediate region 36a may be coated with polyvinylpyrrolidone and/or other hydrophilic coatings, e.g., for the purpose of reducing friction during passage of a device introduced through the hub passage 36 and/or to decrease the adherence of air bubbles to the wall of the passage 36.

The side port 40 includes a first end 42 attached or otherwise coupled to an outer surface of the tubular body 31 adjacent the intermediate region 36b, a second outer end 44, and a port passage 46 extending between the first and second ends 42, 44, thereby defining a port axis 48 extending therebetween. As shown, the port axis 48 intersects the longitudinal axis 38 to define an angle θ, which may define an acute angle between the side port 40 and the proximal end 32 of the tubular body 31, e.g., between about twenty and ninety degrees (20-90°). As shown, the port axis 48 is substantially straight, although alternatively, the port axis 48 may curve or have other shapes corresponding to the side port 40 not being substantially straight, similar to other embodiments herein.

The port passage 46 includes an outlet 47 communicating with the intermediate region 36b of the hub passage 36 such that fluid delivered through the port passage 46 enters the intermediate region 36b of the hub passage 36. Optionally, the second end 44 of the side port 40 may include a luer fitting and/or one or more other connectors and/or valves (not shown), e.g., to accommodate coupling a source of fluid, e.g., a syringe filled with saline and the like (not shown), to the side port 40. In addition or alternatively, a flexible tubular extension (not shown) may be removably or substantially permanently coupled to the second end 44 of the side port 40, e.g., inserted into a recess in the second end 44, received over the second end 44, and then bonded or otherwise attached to the second end 44.

In addition, the side port 40 includes a guide element 60 adjacent the first end 42 for directing fluid introduced into the second end 44 through the port passage 46 into the hub passage 36 in a desired manner. For example, in the embodiment shown, the port passage 46 includes a first inner region 46a adjacent the first end 42 having a first diameter or other cross-section and a second outer region 46b adjacent the second end 44 having a second diameter or cross-section, the first cross-section smaller than the second cross-section. For example, the outer region 46b may include a tapered luer fitting (not shown) having an asymmetric exit port to which another device, e.g., a source of fluid (not shown) may be coupled. Alternatively, the side port 40 may have a substantially uniform cross-section and/or a concentric tapered exit port (not shown), if desired.

The guide element 60 includes a ramped surface 62 within the first inner region 46a immediately adjacent the outlet 47. The ramped surface 62 may be configured to direct at least some fluid introduced through the side port 40 out the outlet 47 towards the proximal end 32 of the tubular body 31, as represented by arrow 64. In this manner, the relatively narrow inner region 46a may accelerate the fluid and the ramped surface 62 may direct the fluid flow proximally, which may enhance flushing air entrapped within the hub passage 36. For example, the accelerated and directed fluid flow may exhibit increased velocity adjacent the walls of the hub passage 36, e.g., in order to dislodge and/or displace collections of air and/or bubbles from the hub passage 36. In addition or alternatively, the ramped surface 62 may have a spiral shape, e.g., extending helically at least partially around the inner wall of the inner region 46a and/or around the port axis 48, e.g., to further accelerate flow and/or direct flow to an area of potentially collected air.

Ideally, the port passage 46, outlet 47, and ramped surface 62 are configured to be moldable using a single pull molding pin (not shown). In the simplest case, the molding pin may be pulled linearly along the axis 48 and the construction of the ramped surface 62 does not preclude this method of fabrication (e.g. does not include undercuts exceeding the elasticity of the molded material). Alternatively, a molding pin may be removed by a combination of rotating and pulling along the axis 48. Other means of fabrication, e.g., 3D printing, may facilitate construction of more complex geometry. For example, the hub 430 shown in FIG. 6 may use a rotational pin pull (not shown), e.g., to provide a side port having a curve, e.g., defining a substantially constant radius of curvature.

For example, a valve member 50 is shown mounted in the tubular body 31 that includes proximal and distal valves 50a, 50b, thereby defining a proximal valve surface 52 adjacent the proximal end 32 and a distal valve surface 54 adjacent the intermediate region 36b of the hub passage 36. At least some fluid from the side port 40 may be directed by the guiding element 60 proximally towards the distal valve surface 54, e.g., to substantially purge any air residing within the intermediate region 36b, e.g., in corners or seams adjacent the valve 50 and/or adherent to the wall of the hub passage 36.

Figure 3:
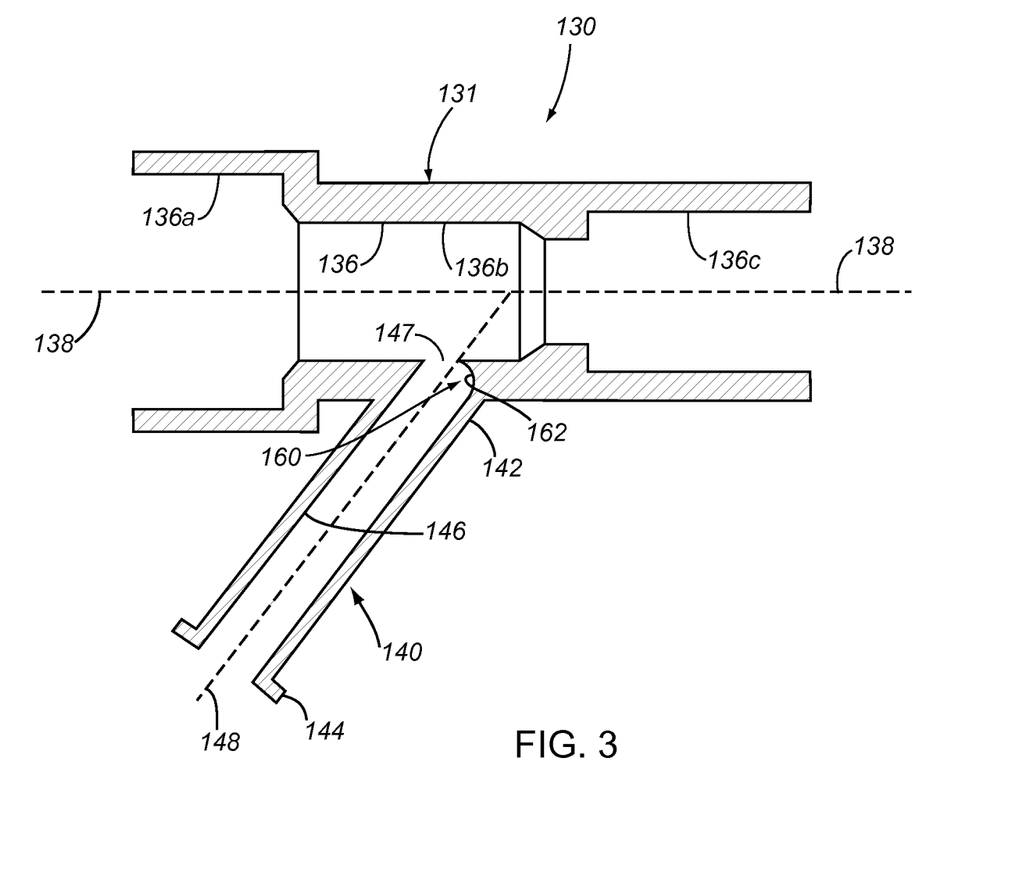
FIG. 3 is a cross-sectional side view of another exemplary embodiment of a hub that may be provided on the proximal end of the tubular device of FIG. 1.

Turning to FIG. 3, another exemplary embodiment of a hub 130 is shown that includes a tubular body 131 and side port 140 including a hub passage 136 and port passage 146, respectively, similar to the hub 30 (with reference nos. for similar features increased by 100 and the valve and tubular member omitted for simplicity). As shown, the port passage 146 has a substantially uniform inner diameter from the outer end 144 towards the inner end 142 until the guiding element 160. The outer end 144 may include a luer fitting, a pocket for receiving an end of a length of tubing, and/or other connector, e.g., to accommodate coupling a source of fluid or other device (not shown) to the side port 140. In this embodiment, the guiding element 160 includes a ramped surface 162 defining a spiral curve, e.g., configured to direct fluid exiting the outlet 147 proximally within the intermediate region 136*b* of the hub passage 136.

Figure 3A:
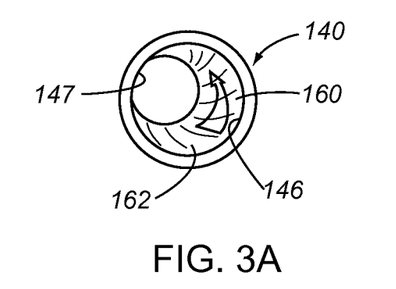
FIG. 3A is a detail showing a view down a side port of the hub of FIG. 3 to show a redirecting element.
Figures 3B, 3C:
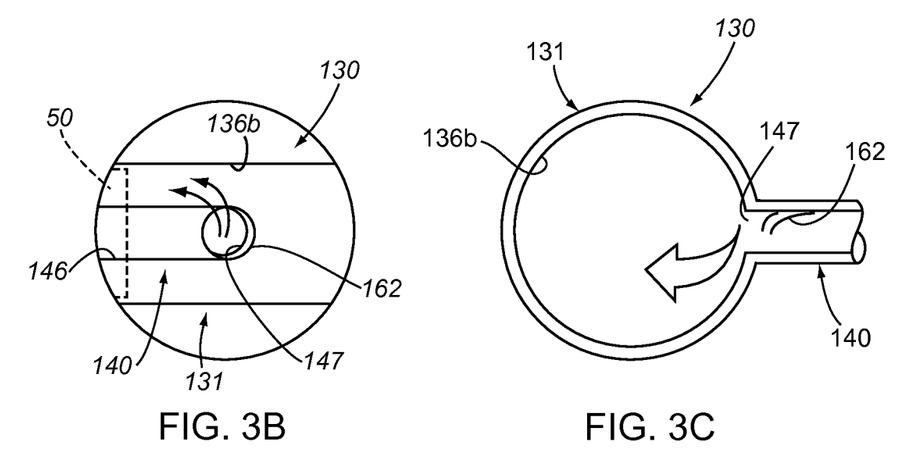
FIGS. 3B and 3C are details of the hub of FIG. 3 showing fluid flowing from a side port into the hub.

FIG. 3A shows a view down the port passage 146 from the outer end 144, showing the ramped surface 162 spiraling away from the outer end in a counterclockwise manner. FIGS. 3B and 3C show exemplary arrows representing fluid flow from the outlet 147 into the intermediate region 136*b* of the hub passage. For example, FIG. 3B is a side detail of the hub 130 and side port 140 showing fluid introduced through the port passage 146 contacting and being redirected by the ramped surface 162 proximally within the intermediate region 136*b* towards the valve 50. FIG. 3C is a cross-sectional view down the hub 130 from the proximal end, showing the fluid spiraling out the outlet 147 clockwise around the intermediate region 136*b* and proximally towards the valve (not shown).

Figure 4A:
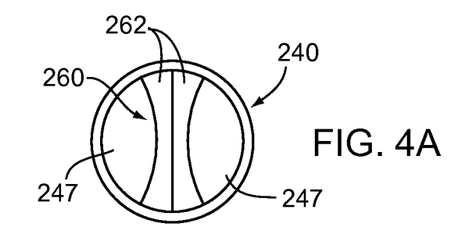
FIG. 4A is a detail showing a view down a side port of a hub showing another embodiment of a redirecting element.
Figure 4B:
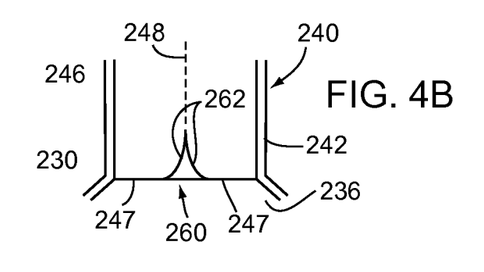
FIG. 4B is a cross-sectional view of the side port of FIG. 4B showing the redirecting element.

FIGS. 4A and 4B show another exemplary embodiment of a redirecting element 260 that may be provided in a side port 240 of a hub 230. As shown, the redirecting element 260 is a divider member extending across the port passage 246 adjacent the inner end 242, thereby defining two outlets 247 communicating with the hub passage 260. The divider member 260 includes a pair of opposite ramped surfaces 262, e.g., having a common leading edge spaced from the outlets 247 and ramping down along the port axis 248 to trailing edges at the respective outlets 247.

The divider member 260 may be oriented in a desired clock position relative to the longitudinal axis of the hub (not shown) to provide a desired flow pattern for fluid from the side port 240 exiting the outlets 247 into the hub passage 260. For example, in one embodiment, the divider member 260 may extend across the side port 240 substantially perpendicular to the longitudinal axis such that the ramped surfaces 262 direct fluid proximally and distally within the hub passage 260. Alternatively, the divider member 260 may extend substantially parallel to the longitudinal axis such that the ramped surfaces 262 direct fluid circumferentially around the inner surface of the hub passage 260.

Figure 5A:
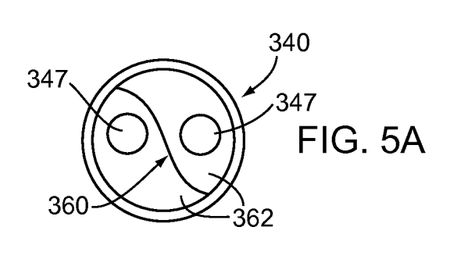
FIG. 5A is a detail showing a view down a side port of a hub showing yet another embodiment of a redirecting element.
Figure 5B:
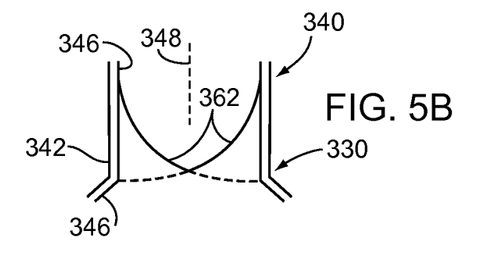
FIG. 5B is a cross-sectional view of the side port of FIG. 5B showing the redirecting element.

FIGS. 5A and 5B show yet another exemplary embodiment of a redirecting element 360 that may be provided in a side port 340 of a hub 330. As shown, the redirecting element 360 is a divider member that spirals across the port passage 346 adjacent the inner end 342, thereby defining two outlets 347 communicating with the hub passage 360. The divider member 360 includes a pair of opposite ramped surfaces 362, e.g., having a common leading edge spaced from the outlets 347 and spiraling down along the port axis 348 to trailing edges at the respective outlets 347.

Figure 6:
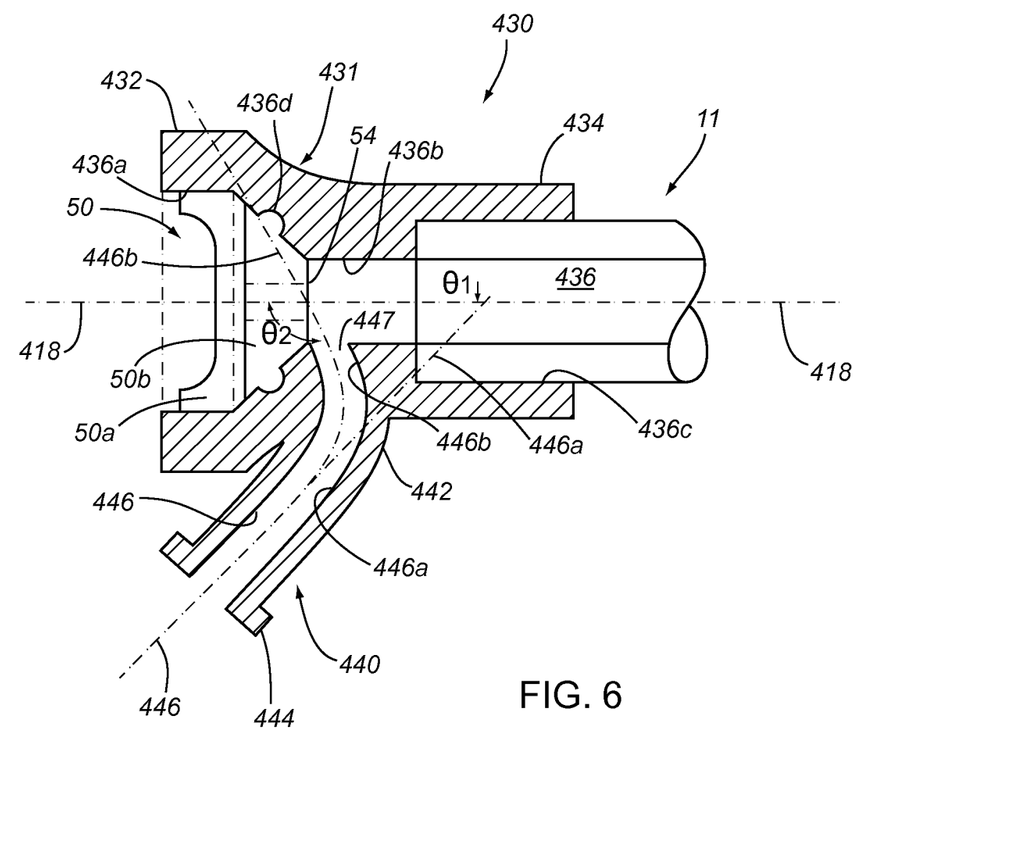
FIG. 6 is a cross-sectional side view of yet another exemplary embodiment of a hub that may be provided on the proximal end of the tubular device of FIG. 1.

Turning to FIG. 6, another exemplary embodiment of a hub 430 is shown that includes a tubular body 431 and side port 440 including a hub passage 436 and port passage 446, respectively, similar to the hub 30 (with reference nos. for similar features increased by 400). The outlet 447 of the port passage 446 enters the hub passage 436 adjacent or nearly adjacent the distal surface 54 of the valve 50.

Unlike the previous embodiments, the port passage 446 may include a non-linear shape that may enhance delivering fluid proximally within the intermediate region 436*b* of the hub passage 436.

As shown, the side port 440 includes an outer section adjacent the outer end 444 defining an outer region 446*a* of the port passage 446 and an inner section adjacent the inner end 442 defining an inner region 446*b* of the port passage 446. For example, as shown, the outer section and region 446*a* may be substantially straight along an outer port axis 446*a* defining a first angle θ1 relative to the longitudinal axis 418, e.g., an acute angle similar to other embodiments herein. Unlike previous embodiments, the inner section and region 446*b* curve such that an inner port axis 446*b* at the outlet 447 defines a second angle θ2 relative to the longitudinal axis 418 that is less acute than the first angle θ1. For example, during molding or other fabrication, a pin formed from an elastic material may be used to shape the port passage 446. Alternatively, a substantially constant radius may be provided, e.g., using a substantially rigid pin having a substantially constant radius of curvature, whereupon the side port 440 would also have a substantially constant radius of curvature. Similar to other embodiments herein, the outer end 444 may include a tapered shape and/or a luer fitting or other connector (not shown).

In one embodiment, the second angle θ2 may be about ninety degrees (90°) such that the inner port axis 446*b* is substantially perpendicular to the longitudinal axis 418. Alternatively, the inner port axis 446*b* may define an obtuse angle relative to the central longitudinal axis 418, e.g., between about ninety and one hundred thirty five degrees) (90-135°) e.g., for directing fluid introduced into the side port 440 through the port passage 446 proximally towards the valve 50.

In addition, the hub 430 may have a relatively short intermediate region 436*b*, e.g., such that the outlet 447 is located immediately adjacent the distal surface 54 of the valve 50. For example, a proximal edge of the outlet 447 may be spaced no more than about four millimeters (4 mm) from the distal surface 54 of the valve 50. Minimizing the space between the outlet 447 and the valve 50 may also minimize the risk of air remaining within the intermediate region 436*b* since corners and/or recesses adjacent the valve 50 are minimized. It will be appreciated that the outlets of other side ports and hubs herein may also be minimized in this manner. Furthermore, where the intermediate region 436*b* is not constructed of the same material and/or does not exhibit the same properties as the inner liner 22 of the tubular member 11, minimizing the space between the between the outlet 447 and the distal surface 54 of the valve 50 may allow a device (not shown) introduced through the bore 436 to more quickly enter the tubular member 11, e.g., avoiding friction that may be encountered passing through the intermediate region 436*b*. In addition or alternatively, where the inner liner 22 of the tubular member 11 includes a hydrophilic or other low surface tension coating or inner surface, air may be more easily displaced during flushing.

Optionally, the hub 430 (or any of the other embodiments herein) may include one or more features to enhance securing the valve 50 within the valve recess 436*a*. For example, in the embodiment shown, the valve 50 includes a substantially cylindrical proximal valve 50*a* and a frustoconical (or otherwise tapered) distal valve 50*b*. The proximal valve 50*a* may include a lead-in (e.g., cup or taper) surface configured to center a device being introduced into the valve 50 and hub 430. The distal valve 50*b* may include an annular ridge, plurality of circumferential tabs, or other retaining features, and the hub 430 may include a corresponding annular groove 436d, recesses, or mating features for receiving the retaining features to enhance engagement between the distal valve 50b and the hub 430.

Figure 7:
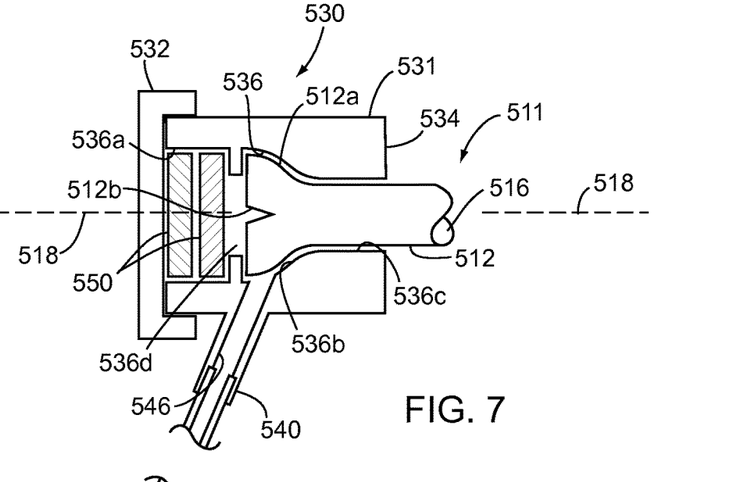
FIG. 7 is a cross-sectional side view of yet another exemplary embodiment of a hub that may be provided on the proximal end of the tubular device of FIG. 1.

Turning to FIG. 7, another exemplary embodiment of a hub 530 is shown that generally includes an elongate main hub portion or tubular body 531 and a side port 540 extending transversely from the tubular body 531. The tubular body 531 includes a proximal end 532, a distal end 534, and a hub passage 536 extending between the proximal and distal ends 532, 534, thereby defining a central longitudinal axis 538, all similar to other embodiments herein. Also similar to other embodiments, the hub passage 536 includes a valve recess 536a adjacent the proximal end 532, an intermediate region 536b, and a distal region 536c aligned generally along the longitudinal axis 538. For example, the valve recess 536a may have a substantially constant diameter shape, e.g., for receiving one or more valve members 550 (two shown), which is separated from the intermediate region 536b by a relatively narrow opening 536d. The intermediate region 536b may taper down to the distal region 536c, e.g., sized to receive the proximal end 512 of a tubular member 511 generally similar to other embodiments herein.

However, as shown, the proximal end 512 of the tubular member 511 may terminate in a flared end 512a including one or more slots 512b (one shown) such that the flared end 512a is disposed immediately adjacent the passage 536d between the intermediate region 536b and the valve recess 536a. The outer diameter of the flared end 512a may be smaller than the inner diameter of the intermediate region 536b, e.g., such than an annular infusion path is defined around the flared end 512a. For example, when fluid is delivered along the port passage 546 to flush the device, the fluid may enter the intermediate region 546b outside the flared end 512a, circulate around the annular region and into the one or more slots 512b into the lumen 516 of the tubular member 511. Optionally, a single slot may be provided that is aligned with the outlet of the port passage 546 to minimize fluid flow within the intermediate region 546b, if desired.

One advantage of the hub 530 is that it may minimize the length of the hub 530 through which a secondary device (not shown) must pass when inserted into the proximal end 532 of the hub 530 into the lumen 516 of the tubular member 511. For example, with the flared end 512a of the tubular member 511 engaged against the narrow opening 546d, a device inserted into the proximal end 532 simply passes through the valve members 550 and directly into the lumen 516 without passing through the intermediate region 536b. The short entry path may also provide less resistance to insertion of the device since the lumen 516 of the tubular member 511 may include a lubricious coating or liner to facilitate insertion. In addition, the annular infusion path may allow the intermediate region 536b to be fully flushed, particularly within the proximal regions closest to the valve passage 536a, which may enhance removal of air trapped in corners within the hub 530.

Figure 8:
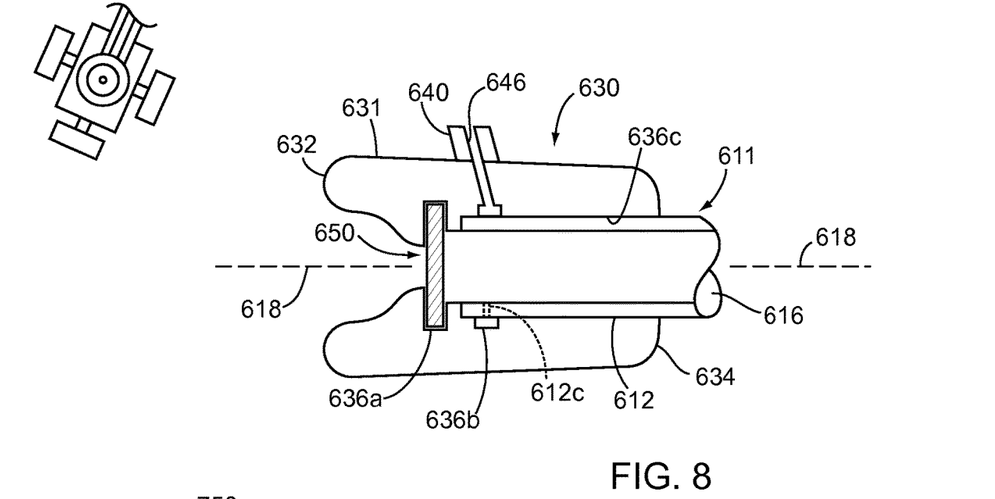
FIG. 8 is a cross-sectional side view of yet another exemplary embodiment of a hub that may be provided on the proximal end of the tubular device of FIG. 1.

Turning to FIG. 8, still another exemplary embodiment of a hub 630 is shown that generally includes an elongate main hub portion or tubular body 631 and a side port 640 extending transversely from the tubular body 631. The tubular body 631 includes a proximal end 632, a distal end 634, and a hub passage 636 extending between the proximal and distal ends 632, 634, thereby defining a central longitudinal axis 638, similar to other embodiments herein. Also similar to other embodiments, the hub passage 636 includes a valve recess 636a adjacent the proximal end 632 and a distal region 636c aligned generally along the longitudinal axis 638.

Unlike the previous embodiments, the hub passage 636 includes an annular manifold or channel 636b that communicates with a port passage 646 of the side port 640. The proximal end 612 of the tubular member 611 may be sized such that the channel 636b is substantially isolated from the other interior regions of the hub 630. The proximal end 612 may include one or more radial passages 612c (one shown) that communicate with the channel 636b such that fluid delivered through the port passage 646 enters the channel 636b and enters the lumen 616 of the tubular member 611 via the passage(s) 612c. In this manner, the fluid path from the side port 640 into the lumen 616 of the tubular member 611 may be minimized, which may facilitate flushing the fluid path to prevent air from remaining within the fluid path after the device is flushed.

Figure 9:
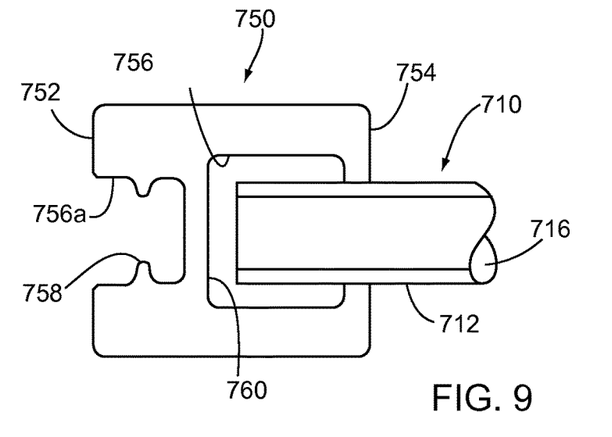
FIG. 9 is a cross-sectional side view of a valve member that may be provided on the proximal end of the tubular device of FIG. 1.

Turning to FIG. 9, another exemplary embodiment of a valve member 750 is shown that may be provided on a proximal end 712 of a tubular member 710, which may be similar to the other embodiments described elsewhere herein. The valve member 750 may include one or more valve elements, e.g., molded or otherwise formed from flexible materials, such as silicone or other elastomers. The valve member 750 may be secured to or contained within a rigid or semi-rigid casing or other structure (not shown), which may be attached or otherwise coupled to the proximal end 712 to support the valve member 750.

The valve member 750 may include a plurality of valve elements that may accommodate inserting one or more devices (not shown) into the lumen 716 of the tubular member 711 while providing a substantially fluid-tight seal both without the device(s) and with the device(s) inserted through the valve member 750 into the lumen 716. For example, the valve member 750 may include a valve passage 756 extending between proximal and distal ends 752, 754 of the valve member 750 and a plurality of features extending into and/or across the valve passage 756 to provide various sealing functions. For example, an annular ridge 758 may be provided in a first or proximal region 756a of the valve passage that defines an inner diameter corresponding to the outer diameter of a primary instrument that may be introduced into the lumen 716, e.g., such that the instrument slidably and/or sealingly engages the ridge 758.

In addition, the valve member 750 may include a closed valve element 760, e.g., a panel that extends entirely across the valve passage 756 in a relaxed state to prevent substantial fluid flow through the valve passage 756 when no instrument is inserted into the valve member 750. The closed valve element 760 may include a slot, a flap, and/or other elements (not shown), e.g., similar to the valves described in the references incorporated by reference elsewhere herein, which may open to accommodate an instrument and resiliently return to the closed position. Optionally, the valve member 750 may be included in any of the hubs described herein.

With any of the embodiments herein, the hub may be integrally formed together as a single piece or may be formed separately and then attached together to provide the hub. For example, with reference to the hub 30 of FIG. 2, the tubular body 31 and side port 40 including the guiding element 60 may be injection molded, cast, or otherwise formed as a single piece. Alternatively, the tubular body 31 and side port 40 may be formed separately, e.g., by extrusion, injection molding, casting, and the like, and attached to each other, as desired, e.g., using cooperating connectors (not shown), bonding with adhesive, fusing, sonic welding, heat bonding, reflowing, insert molding, and the like. The hub 30 and/or its components may be formed from plastic, metal, or composite materials, as desired, such as nylon, PEBAX, PTFE, HDPE, PVC, polycarbonate, and the like.

Once the hub 30 is formed, a valve 50 may be secured in the valve recess 36a and/or otherwise to the hub 30. In an exemplary embodiment, the valve 50 may include a pair of valve members, e.g., proximal and distal valves 50a, 50b, that include complementary passages that provide a substantially fluid-tight seal (to prevent blood from escaping from and/or air from entering the hub 30) yet accommodate insertion of one or more instruments through the hub 30. In an exemplary embodiment, each valve 50a, 50b may include a transverse slot extending partially across the faces of the valve (and extending between the opposite ends of the valve), with the valves installed offset from one another, e.g., by about ninety degrees (90°) such that slots cross one another.

Alternatively, a single valve 50 may be provided that includes a sequence of passages therethrough. For example, in one embodiment, the valve body 50 may be integrally formed as a single piece, e.g., by injection molding, casting, and the like. Alternatively, the valve body may be formed as a solid body and one or more features, e.g., passages, connectors, and the like (not shown) may be formed into the solid body, e.g., by cutting, machining, and the like.

Whether including one or more components, the valve 50 may be formed from an elastomeric material, such as silicone, chronoprene, isoprene, santoprene, and the like. Exemplary embodiments of valves that may be used are disclosed in U.S. Pat. Nos. 8,317,754 and 8,512,293, the entire disclosures of which are expressly incorporated by reference.

The valve 50 may be secured within the valve recess 36a by interference fit. In addition or alternatively, the valve 50 may be secured to the hub 30 using other methods, e.g., at least one of bonding with adhesive, welding, fusing, one or more connectors, (not shown), and the like.

A tubular device 11 may be attached to the distal end of the hub 30, e.g., using conventional methods. For example, the proximal end 12 of the tubular device 11 may be inserted into the distal region 36c of the hub 30 and secured by one or more of interference fit, bonding with adhesive, welding, fusing, one or more connectors, (not shown), and the like.

During use, the apparatus 10 may be used for delivering a medical device into a body lumen within a patient's body, e.g., a lead, catheter, and the like, into a patient's vasculature, heart, or other body lumen, as described above. Before use, a source of fluid, e.g., a syringe of saline (not shown) may be coupled to the second end 44 of the side port 40 and fluid delivered through the port passage 46 to flush the apparatus 10. The redirecting element 60 may enhance fluid being directed proximally towards the valve 50 rather than simply passage through the distal region 36c into the lumen 16 of the tubular device 11, which may enhance removing air or any other undesirable materials residing within the hub passage 36, particularly in the intermediate region 36b adjacent the distal surface 54 of the valve 50.

Once sufficiently flushed, the apparatus may introduced into a patient's body. For example, a distal end 14 of the tubular member 11 may be introduced into a patient's vasculature with the hub 30 and valve 50 remaining outside the patient's body. The tubular member 11 may be advanced through the patient's vasculature, e.g., to position the distal end 14 and a desired location, e.g., a coronary vein within the patient's heart or other body lumen. A medical device, e.g., a pacing or other electrical lead, a guidewire, and/or other instrument (not shown), may be inserted through the valve 50 and hub 30 and into the tubular member 11 until a distal end of the medical device is advanced into the body lumen, e.g., exiting or remaining within the distal end 14 of the tubular member 11.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A hub for a sheath, catheter, or other tubular device, comprising:
    a tubular body comprising a proximal end, a distal end, and a hub passage extending between the proximal end and the distal end;
    a valve mounted in the tubular body adjacent the proximal end comprising a proximal surface adjacent the proximal end and a distal surface adjacent an intermediate region of the hub passage;
    a side port comprising a first end coupled to an outer surface of the tubular body adjacent the intermediate region, a second outer end, and a port passage extending between the second outer end and the first end and communicating with the intermediate region of the hub passage; and
    a guide element in the side port adjacent the first end for directing fluid introduced into the second outer end through the port passage towards the distal surface of the valve,
    wherein the port passage comprises a first inner region adjacent the first end having a first cross-section and a second outer region adjacent the second end having a second cross-section, the first cross-section smaller than the second cross-section, and wherein the guide element comprises a ramped surface within the first inner region, and
    wherein the port passage defines a central axis extending through the port passage between the first and second ends, and wherein the ramped surface extends helically relative to the central axis.

2. The hub of claim 1, wherein the port passage defines a central axis extending through the port passage between the first and second ends, and wherein the ramped surface includes an inner edge adjacent the hub passage oriented to deflect fluid introduced into the second end through the port passage away from the central axis towards the proximal end within the hub passage.

3. A hub for a sheath, catheter, or other tubular device, comprising:
  a tubular body comprising a proximal end, a distal end, a hub passage extending between the proximal end and the distal end, and a longitudinal axis between the proximal end and the distal end;
  a valve mounted in the tubular body adjacent the proximal end for providing a substantially fluid-tight while accommodating inserting an instrument into the proximal end into the hub passage, the valve comprising a proximal surface adjacent the proximal end and a distal surface adjacent an intermediate region of the hub passage; and
  a side port comprising a first end coupled to an outer surface of the tubular body adjacent the intermediate region, a second outer end, and a port passage extending between the second outer end and the first end and communicating with the intermediate region of the hub passage,
  wherein the port passage comprises a first inner region adjacent the first end defining a first port axis and a second outer region adjacent the second outer end defining a second port axis, the second port axis defining an acute second angle relative to the longitudinal axis and proximal end of the tubular body, the first port axis defining a first angle relative to the longitudinal axis that is less acute than the second angle,
  wherein the first end of the side port defines an outlet adjacent the distal surface of the valve, and
  wherein a proximal edge of the outlet is spaced no more than about four millimeters (4 mm) from the distal surface of the valve.

4. The hub of claim 3, wherein the first port axis is perpendicular to the longitudinal axis.

5. The hub of claim 3, wherein the first port axis is obtuse relative to the longitudinal axis and the proximal end of the tubular body for directing fluid introduced into the second end through the port passage proximally towards the distal surface of the valve.

6. A hub for a sheath, catheter, or other tubular device, comprising:
  a tubular body comprising a proximal end, a distal end, and a hub passage extending between the proximal end and the distal end;
  a valve mounted in the tubular body adjacent the proximal end comprising a proximal surface adjacent the proximal end and a distal surface adjacent an intermediate region of the hub passage;
  a side port comprising a first end coupled to an outer surface of the tubular body adjacent the intermediate region, a second outer end, and a port passage extending between the second outer end and the first end and communicating with the intermediate region of the hub passage; and
  a guide element in the side port adjacent the first end for directing fluid introduced into the second outer end through the port passage towards the distal surface of the valve,
  wherein the port passage defines a central axis extending through the port passage between the first and second ends and includes an outlet communicating with the hub passage, and wherein the guide element comprises a flow divider extending across the outlet for dividing flow of fluid introduced into the second end through the port passage into the hub passage.

7. The hub of claim 6, wherein the guide element comprises a proximal ramped surface for directing a portion of fluid passage through the outlet proximally towards the valve distal surface and a distal ramped surface for directing a portion of fluid passage through the outlet distally towards the distal end of the hub.

8. The hub of claim 6, wherein the flow divider comprises first and second spiral surfaces dividing the outlet into first and second openings.

9. The hub of claim 6, wherein the hub passage comprises a proximal valve recess extending from the proximal end to the intermediate region of the tubular body, and wherein the intermediate region has a smaller cross-section than the valve recess.

10. The hub of claim 9, wherein the hub passage comprises a distal region adjacent the distal end for receiving a portion of the tubular device therein and a tapered region between the intermediate region and the distal region.

11. The hub of claim 10, wherein the valve comprises one or more valve members for providing a seal to prevent substantial flow through the proximal end while accommodating inserting an instrument into the proximal end and through the hub passage.

\* \* \* \* \*